United States Patent [19]

Murtha

[11] 4,166,772

[45] Sep. 4, 1979

[54] EXTRACTIVE DISTILLATION SEPARATION OF CUMENE AND PHENOL

[75] Inventor: Timothy P. Murtha, Bartlesville, Okla.

[73] Assignee: Phillips Petroleum Company, Bartlesville, Okla.

[21] Appl. No.: 949,297

[22] Filed: Oct. 6, 1978

[51] Int. Cl.$^2$ .................. B01D 3/40; C07C 37/38
[52] U.S. Cl. .................................. 203/60; 203/84; 568/754; 568/757
[58] Field of Search .................. 203/50, 60, 84, 38, 203/57; 568/749, 754, 757

[56] References Cited

U.S. PATENT DOCUMENTS

| | | | |
|---|---|---|---|
| 2,171,795 | 9/1939 | Kautter | 203/60 |
| 2,663,743 | 12/1953 | Bewley et al. | 568/754 |
| 2,884,361 | 4/1959 | Bloom et al. | 203/60 |
| 3,169,101 | 2/1965 | Berthoux | 203/63 |
| 3,285,973 | 11/1966 | Aria | 568/757 |
| 3,492,362 | 1/1970 | Neltesheim | 203/60 |
| 4,115,207 | 9/1978 | Murtha | 203/60 |

*Primary Examiner*—Wilbur L. Bascomb, Jr.

[57] ABSTRACT

A trisubstituted phosphate is employed as extractive distillation solvent in the separation of cumene and phenol.

4 Claims, No Drawings

EXTRACTIVE DISTILLATION SEPARATION OF CUMENE AND PHENOL

This invention relates to extractive distillation. In one of its aspects it relates to an extractive distillation process for the separation of cumene and phenol employing an extractive distillation solvent.

In one of its concepts the invention provides an extractive distillation process which comprises employing as extractive distillation solvent a trisubstituted phosphate. In another of its concepts the invention provides an extractive distillation process for the separation of substantially pure cumene from a mixture containing it and phenol by subjecting the mixture to extractive distillation in an extractive distillation zone in which a trisubstituted phosphate is employed as an extractive distillation solvent and from which there is recovered as overhead the substantially pure cumene and as bottoms a solvent containing phenol. Further, in another of its concepts, the invention provides a process in which at least a portion of the phenol is removed from the solvent by distillation and the solvent is returned to the extractive distillation for reuse.

Cumene can be converted to phenol and acetone via cumene hydroperoxide. The acid catalyzed cleavage of cumene hydroperoxide in the presence of unoxidized cumene results in a mixture of cumene, phenol and acetone. Separation of this mixture by conventional techniques including fractional distillation results in a cumene-phenol azeotrope containing 2 weight % phenol. Cumene free of phenol is required for recycle to the cumene oxidation stage because the presence of phenol is detrimental to the oxidation reaction.

It is an object of this invention to provide an extractive distillation process. Another object of the invention is to provide a solvent suitable for extractive distillation use. A further object of the invention is to provide a process for the separation of cumene and phenol. A still further object of the invention is to provide a process of extractive distillation for the recovery of substantially pure cumene from a mixture containing it and phenol.

Other aspects, concepts and the several advantages of the invention are apparent from a study of this disclosure and the claims.

According to the present invention a mixture of cumene and phenol is separated to produce substantially pure cumene by subjecting the mixture to an extractive distillation in the presence of a trisubstituted phosphate.

Also according to the invention the trisubstituted phosphate solvent which contains phenol after use is subjected to a further separation as by distillation to recover therefrom at least some of the phenol therein contained whereupon the solvent is returned for reuse in the extractive distillation step.

In the practice of the process of this invention, cumene containing as much as about 50 wt. % phenol can be utilized. It is within the scope of this invention to remove by suitable techniques, such as fractional distillation, a portion of the phenol. Normally, cumene containing from about 2 to about 20 wt. % phenol and preferably from about 2 to about 10 wt. % phenol is utilized in the extractive distillation step.

Any alpha-methylstyrene present in the mixture can be removed by hydrogenation using known techniques.

The trisubstituted phosphate solvent to be used in the extractive distillation of this invention contain up to 30 carbon atoms and are represented by the following general formula: $(RO)_3PO$ wherein each R is selected from a group consisting of alkyl radicals containing 4 to 18 carbon atoms, cycloalkyl radicals containing 5 to 12 carbon atoms, aryl or substituted aryl radicals containing 6 to 18 carbon atoms with the substituent groups being one or more or a mixture of alkyl, cycloalkyl, alkoxy, halogen, or the like, and aralkyl radicals containing 7 to 12 carbon atoms. The phosphate solvents preferably should oil above the boiling point of phenol (182° C. at atmospheric pressure) to facilitate the separation of the solvent for recycling by fractional distillation. Low levels of phenol (up to about 10 wt. % phenol) can be present in the recovered and recycled solvent with no detrimental effects on the extractive distillation. For ease of handling, solvents generally preferred are liquid or a low melting (below about 80° C.) solid.

Specific examples of trisubstituted phosphates that are suitable for the extractive distillation of this invention include tributyl phosphate, trihexyl phosphate, tricyclohexyl phosphate, tribenzyl phosphate, triphenyl phosphate, tricresyl phosphate (mixed o, m, and p isomers), tri-m-tolyl phosphate, tri-p-tolyl phosphate, tri-p-chlorophenyl phosphate, diphenylcresyl phosphate, and the like and mixtures thereof. These compounds are either commercially available or can be prepared by known methods. For example, the reaction of phenol with phosphorous oxychloride ($POCl_3$) yields triphenyl phosphate. The currently preferred solvents for the extractive distillation of this invention are tricresyl phosphate (prepared from mixed isomers) and triphenyl phosphate.

The extractive distillation of this invention can be carried out under a variety of conditions. The volume ratio of trisubstituted phosphate solvent to feedstream will be broadly from about 0.01/1 to about 25/1, preferably 0.1/1 to 5/1. The pressure utilized in the extractive distillation of this invention can be atmospheric or subatmospheric. The temperature used will depend on the pressure and on the specific solvent used and can be readily determined by one skilled in the art.

A feed mixture containing phenol and cumene is fed to an extractive distillation column. A trisubstituted phosphate solvent is introduced into the extractive distillation column at a point above the point of introduction of the feed mixture. The overhead stream from the extractive distillation column is cumene substantially freed of phenol. The bottom stream, which contains phenol and trisubstituted phosphate, is withdrawn from the extractive distillation column and passed to a distillation column. In the distillation column, the phenol-trisubstituted phosphate mixture is separated into an overhead stream containing phenol and a bottom stream containing the trisubstituted phosphate solvent. The recovered trisubstituted phosphate can be recycled to the extractive distillation column.

In the following examples, extractive distillations were conducted in an electrically heated 0.75 inch (19 mm) diameter ×36 inch (914 mm) length column containing 0.25 inch (6.4 mm) Por-Pak stainless steel perforated screen packing. The solvent was fed through a rotameter and a heating section to an introduction port 3 inches (76 mm) from the top of the column. The mixture to be separated was fed through a rotameter and a heating section to an introduction port 18 inches (457 mm) from the top of the column. The overhead product was collected and analyzed by gas-liquid chromotography (glc) on a Hewlett-Packard 5710A chromatograph equipped with a flame ionization detector.

The cumene-phenol mixture to be separated in the following examples was prepared from commercially available materials and contained about 4.7 wt. % phenol. The tricresyl phosphate was a commercially available material prepared from mixed cresols.

EXAMPLE I

An extractive distillation run was carried out according to the process of this invention utilizing tricresyl phosphate as the extractive distillation solvent. Cumene containing about 4.7 wt. % phenol was fed through the lower introduction port of the distillation column at a rate of about 37 ml/hr. The tricresyl phosphate solvent was fed through the upper introduction port of the distillation column at a rate of about 45 ml/hr for a solvent/feed volume ratio of about 1.22/1. The extractive distillation conditions were 103 mm Hg pressure and 70°-71° C. head temperature. Over a 5 hour run time, the overhead fractions contained substantially pure cumene containing only 0.03 weight % phenol. The cumene collected was about 88 wt. % of the amount of cumene fed to the column during the run. The results of this run demonstrates the removal of phenol from a phenol-cumene mixture by an extractive distillation with tricresyl phosphate.

EXAMPLE II

Another run was carried out according to this invention utilizing tricresyl phosphate as the extractive distillation solvent. This extractive distillation was conducted in a manner similar to the run in Example I except the feed rate was about 27 ml/hr, the solvent/feed ratio was about 0.66/1, the head temperature was 65°-68° C., and the pressure was 100 mm Hg. Over a 3.75 hour run time, the overhead cumene fractions contained only 0.04 wt. % phenol. The cumene collected during the run was 83 wt. % of the cumene fed to the column during the run.

The results of this run demonstrate the removal of phenol from a phenol-cumene mixture by the process of this invention.

Reasonable variation and modification are possible within the scope of the foregoing disclosure and the appended claims to the invention the essence of which is that a trisubstituted phosphate, e.g., tricresyl phosphate, has been found to be an efficient extractive distillation solvent for the extractive distillation separation of cumene and phenol containing mixtures.

I claim:

1. An extractive distillation process for the separation of cumene and phenol from a mixture containing the same which comprises utilizing as extractive distillation solvent a trisubstituted phosphate.

2. A process according to claim 1 wherein cumene is recovered as overhead and the trisubstituted phosphate solvent containing phenol is removed from the extractive distillation zone as a bottom stream.

3. A process according to claim 2 wherein the bottom stream is subjected to distillation to remove at least a portion of the phenol therefrom following which the solvent, thus treated, is returned to the extractive distillation zone for reuse.

4. A process according to claim 1 wherein the extractive distillation solvent is tricresyl phosphate.

* * * * *